United States Patent [19]

Röhrscheid

[11] Patent Number: 5,175,351
[45] Date of Patent: Dec. 29, 1992

[54] PROCESS FOR THE PREPARATION OF ALKANESULFONYLBENZOIC ACIDS

[75] Inventor: Freimund Röhrscheid, Kelkheim, Fed. Rep. of Germany

[73] Assignee: Hoechst Aktiengesellschaft, Frankfurt am Main, Fed. Rep. of Germany

[21] Appl. No.: 856,470

[22] Filed: Mar. 24, 1992

[30] Foreign Application Priority Data

Mar. 26, 1991 [DE] Fed. Rep. of Germany ....... 4109819

[51] Int. Cl.⁵ .............................................. C07C 51/16
[52] U.S. Cl. .................... 562/414; 562/416
[58] Field of Search ..................... 562/414, 416, 429

[56] References Cited

U.S. PATENT DOCUMENTS

| | | | |
|---|---|---|---|
| 3,504,022 | 3/1970 | Bresson | 562/416 |
| 3,692,828 | 9/1972 | Onopchewko | 260/524 |
| 4,503,245 | 3/1985 | Giacobbe | 562/416 |
| 4,704,467 | 11/1987 | Wehrenberg | |
| 4,914,231 | 4/1990 | Manami et al. | |
| 4,954,165 | 9/1990 | Baba | 562/429 |
| 5,087,724 | 2/1992 | Tanaka | 562/429 |

FOREIGN PATENT DOCUMENTS

| | | | |
|---|---|---|---|
| 0203428 | 12/1986 | European Pat. Off. | |
| 2-174746 | 7/1990 | Japan | 562/416 |
| 90-13537 | 11/1990 | World Int. Prop. O. | |

OTHER PUBLICATIONS

Hiroshi, S. et al, *Chemical Abs.* 111:133781n Abstract of JP 01-79145 (1989).

*Primary Examiner*—Michael L. Shippen

[57] ABSTRACT

A process for the preparation of alkanesulfonylbenzoic acids from alkanesulfonylalkylbenzenes of the formula

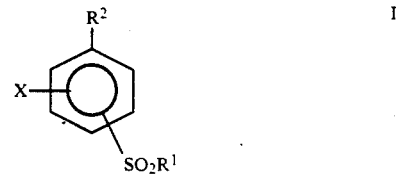

in which $R^1$ and $R^2$ are identical or different and are alkyl having 1 to 4 carbon atoms, but $R^2$ has a meaning other than t-butyl, and X is H, F, Cl, Br or $NO_2$, using molecular oxygen in acetic acid and/or propionic acid in the presence of a catalyst containing cobalt and bromine ions and, in particular when the meaning of $R^2$ is other than methyl, also manganese ions, which is additionally carried out in the presence of metal ions of Main Group 2 and/or 3.

20 Claims, No Drawings

PROCESS FOR THE PREPARATION OF ALKANESULFONYLBENZOIC ACIDS

DESCRIPTION

The invention relates to an improved process for the preparation of alkanesulfonylbenzoic acids from the corresponding alkanesulfonylalkylbenzenes using molecular oxygen in acetic acid and/or propionic acid.

Alkanesulfonylbenzoic acids are precursors for pesticides and herbicides (U.S. Pat. No. 4,704,467, EP-OS 203,428).

WO 90/13537 describes a process for oxidizing optionally substituted alkanesulfonylalkylbenzenes using molecular oxygen in acetic acid or propionic acid to give the corresponding alkanesulfonylbenzoic acids. The oxidation is carried out in the presence of a catalyst which is soluble in the acid and which contains cobalt and bromide ions and, if appropriate, manganese ions, under increased pressure at temperatures of above 120° C.

Depending on the concentration, the alkanesulfonylbenzoic acids crystallize from the reaction solution on cooling and are separated by filtration. The filtrate contains the catalyst and substantial amounts of dissolved product. This is why, in a preferred embodiment, the water formed during the reaction is removed from the filtrate, and this mother liquor is recycled as reaction medium for the next oxidation.

It was therefore an object of the present invention to provide a process for the preparation of alkanesulfonylbenzoic acids which yields in particular alkanesulfonylbenzoic acids in high yield and high purity and allows problem-free recycling of the mother liquor.

Surprisingly, it has now been found that alkanesulfonylbenzoic acids can be prepared in a simple manner from alkanesulfonylalkylbenzenes of the formula I (see patent claim 1) in which $R^1$ and $R^2$ are identical or different and are alkyl having 1 to 4 carbon atoms, but $R^2$ has a meaning other than t-butyl, and X is H, F, Cl, Br or $NO_2$, using molecular oxygen in acetic acid and/or propionic acid in the presence of a catalyst containing cobalt and bromide ions and, in particular when the meaning of $R^2$ is other than methyl, also manganese ions, when the reaction is additionally carried out in the presence of metal ions of Main Group 2 and/or 3.

The metal ions are preferably added in the form of the salts of the carboxylic acid in question. The bromide can be added in the form of an HBr solution or, expediently, in the form of magnesium bromide, calcium bromide, cobalt bromide or manganese bromide. Suitable metal ions of Main Group 2 and 3 are, in particular, those of magnesium, calcium, strontium, barium and aluminum, but preferably $Mg^{2+}$ and in particular $Ca^{2+}$.

The use of calcium acetate in the oxidation of 2-chloro-4-methanesulfonyltoluene (cf. Examples) allows the mother liquor to be recycled for example nine times, while maintaining the activity of the catalyst. After washing with glacial acetic acid, the product is colorless and can be washed with water without the wastewater being contaminated by cobalt or manganese ions.

At the beginning of each oxidation, the molar ratio of the total of the metal ions of Main Group 2 and/or 3 to the total of cobalt and, if appropriate, manganese ions is expediently (0.1 to 10):1, preferably (0.3 to 3):1, and, in particular, (0.5 to 1.5):1, the amount of metal ions of Main Group 2 and/or 3 expediently being 1 to 5 mol % of the alkanesulfonylalkylbenzene.

Suitable alkyl groups for $R^1$ and $R^2$ are in each case methyl, ethyl, n- and iso-propyl, n-, sec- and iso-butyl, and for $R^1$ additionally also t-butyl. During the oxidation, the radical $R^2$ is oxidized to give the COOH group. The oxidation of the methyl group $R^2$ requires 1.5 mol of oxygen.

The starting compounds are readily accessible; alkanesulfonyltoluenes can be prepared, for example, from toluenesulfonic acid by reduction to give sodium toluenesulfinates or by reaction with dimethyl sulfate or diethyl sulfate.

The present process is advantageously carried out under conditions which are particularly effective for the oxidation of alkyl groups and which are used, for example, for the oxidation of the two methyl groups of p-xylene to give terephthalic acid. The use of these highly effective oxidation conditions allows the alkyl group to be oxidized on the benzene ring, even when the benzene ring additionally to the highly electron-attracting alkanesulfonyl group carries an additional, deactivating substituent X. However, it is surprising that only the alkyl group is oxidized on the benzene ring under these oxidation conditions, while the alkanesulfonyl group remains unchanged. For example, in contrast to the alkanesulfonyl group, the acetyl group of acetophenone is readily degraded by oxidation under these conditions.

In general, acetic acid and/or propionic acid are used in anhydrous form; however, water is formed during the oxidation. However, the reaction system generally does not contain more than 15% of water, in particular a maximum of 5%. The use of anhydrous acetic acid is preferred.

The presence of manganese ions is necessary for the desired oxidation of the ethyl, propyl and butyl group bonded to the aromatic ring, but is also expedient for the oxidation of the methyl group, even though a combination of metal ions of Main Group 2 and/or 3, cobalt and bromine ions suffices for the latter purpose. The presence of manganese ions allows the amount of cobalt required to be reduced, while maintaining the activity of the catalyst.

In general, the ratio of the concentration of cobalt to manganese ions is 1:(0.2 to 3), preferably 1:(0.3 to 1.2). The ratio of the total of the concentration of the cobalt and manganese ions to bromine ions is expediently 1:(0.01 to 2), preferably 1:(0.1 to 1), particularly preferably 1:(0.2 to 0.7). The total of the concentrations of cobalt and manganese ions is expediently in the range of 0.01 to 0.2 mol, preferably 0.02 to 0.15 mol and, in particular, 0.04 to 0.12 mol of metal ions per 1 of the liquid phase.

The molecular oxygen is preferably introduced into the liquid reactor phase in the form of dry air. The process is expediently carried out at an oxygen partial pressure of 1.5 to 8, preferably 2.4 to 7 and, in particular, 2.8 to 6, bar. The reaction temperature is expediently in the range of 120° to 220° C., preferably 130° to 180° C., and, in particular, 135° to 160° C.

To achieve complete and rapid oxidation of the alkyl group on the benzene ring, it is especially advantageous to use a catalyst concentration of 0.04 to 0.12 mol of cobalt and manganese ions per 1 of liquid phase and to apply a high oxygen partial pressure of at least 2.4 to 2.5 bar at the point where the oxygen enters the liquid phase. The combination of these two measures also allows the reaction temperature required to be kept low. If no extremely severe conditions are combined, the alkanesulfonyl group is attacked by oxidation to a negligible extent only.

Depending on the concentration, the alkanesulfonyl acids crystallize from the reaction solution on cooling and can be separated by filtration. However, the filtrate frequently contains substantial amounts of dissolved product and the entire catalyst. An advantageous embodiment of the process therefore provides that the water formed during the reaction is separated from the filtrate on a column and that this mother liquor is recycled as reaction medium for the next oxidation. This saves catalyst, the waste water is not contaminated unduly, and the isolated yield of the subsequent batch is higher.

In the examples which follow, "OAc" is acetate.

EXAMPLES

1. In a 1 l stainless steel autoclave equipped with thermometer, stirrer, reflux condenser and pressure-maintaining valve, a mixture of 250 g of 2-chloro-4-methanesulfonyltoluene, 15 g of Co(OAc)$_2$.4H$_2$O, 10 g of Ca(OAc)$_2$, 2 g of a 62% aqueous hydrogen bromide solution and 455 g of glacial acetic acid was heated to 150° C. under a pressure of 16 bar nitrogen. Air (16 bar) was then passed into the liquid phase by means of a dip tube. The exothermic reaction started immediately, and the temperature was kept at 155° to 160° C. by means of cooling. The oxygen content in the exit gas was kept at 5 to 6% by volume by controlling the air supply. When the exothermic reaction had finished, the hot reaction solution was withdrawn and cooled to 20° C., with stirring. The crystals which had precipitated were filtered off with suction, washed four times using 50 ml portions of glacial acetic acid and three times using 75 ml portions of water, and dried at 80° C. and 65 mbar in a gentle stream of air.

Yield: 248.0 g (86.5% of theory) of 2-chloro-4-(methanesulfonyl)benzoic acid; m.p. 193° to 194° C.

2. The filtrate and the liquid from Example 1 which had been obtained during washing with acetic acid were distilled off in a column under atmospheric pressure. The water was separated off first, and such an amount of acetic acid was then distilled off that approx. 440 g of solution remained in the distillation flask. The bottom temperature was 121° C.

A 1 l oxidation autoclave was charged with a mixture of 204.7 g of 2-chloro-4-methanesulfonyltoluene, 2.3 g of Ca(OAc)$_2$, 1.9 g of a 62% aqueous HBr solution and the concentrated mother liquor (440 g). Oxidation and workup were as in Example 1.

Yield: 220.7 g (94.1% of theory) of 2-chloro-4-(methanesulfonyl)benzoic acid, m.p. 192° to 193° C.

3. to 10. Example 2 was repeated eight times, in each case using the mother liquor of the previous batch from which water had been removed.

The average yield in Examples 3 to 10 was 219.7 g (93.6% of theory), m.p. 191° to 193° C.

I claim:

1. A process for the preparation of alkanesulfonylbenzoic acids from alkanesulfonylalkylbenzenes of the formula

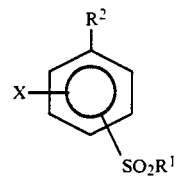

in which $R^1$ and $R^4$ are identical or different and are alkyl having 1 to 4 carbon atoms, but $R^2$ has a meaning other than t-butyl, and X is H, F, Cl, Br or NO$_2$, using molecular oxygen in acetic acid and/or propionic acid in the presence of a catalyst containing cobalt and bromine ions and, optionally also manganese ions, which is additionally carried out in the presence of metal ions of Main Group 2 and/or 3.

2. The process as claimed in claim 1, wherein acetic acid is used.

3. The process as claimed in claim wherein magnesium, calcium, strontium, barium or aluminum ions, are employed as metal ions of Main Group 2 and/or 3.

4. The process as claimed in claim 3, wherein the Ca$^{2+}$ is introduced in the form of calcium acetate.

5. The process as claimed in claim 1,
wherein the molar ratio of the total of the metal ions of Main Group 2 and/or 3 and the total of cobalt and/or manganese ions is (0.1 to 10):1.

6. The process as claimed in claim 5, wherein the amount of metal ions of Main Group 2 and/or 3 is 1 to 5 mol % of the alkanesulfonylalkylbenzene.

7. The process as claimed in claim
wherein the oxygen partial pressure in the reactor is 1.5 to 8, bar.

8. The process as claimed in claim 1,
where the reaction temperature is 120° to 220° C., 9. The process as claimed in claim 1,
wherein a crystalline product which has precipitated is separated off and the mother liquor is recycled as reaction medium.

10. The process as claimed in claim 1, wherein the catalyst also contains manganese ions.

11. The process as claimed in claim 1
wherein cobalt and manganese ions are use in a concentration ratio of 1:(0.2 to 3).

12. The process as claimed in claim 10,
wherein the ratio of the total of the concentrations of cobalt and manganese ions and the concentration of the bromine ions is 1:(0.01 to 2).

13. The process as claimed in claim 10,
wherein the total of the concentrations of cobalt and manganese ions is 0.01 to 0.2 mol, metal ions per 1 of liquid phase.

14. The process as claimed in claim 10, wherein $R^2$ in formula I is an alkyl group other then methyl.

15. The process as claimed in claim 1, wherein Mg$^{2+}$, Ca$^{2+}$, or combinations thereof are said metal ions of Main Group 2 and/or 3.

16. The process as claimed in claim 5, wherein said molar ratio is (0.3 to 3):1.

17. The process as claimed in claim 10, wherein the molar ratio of the total of the metal ions of Main Group 2 and/or 3 and the total of cobalt and/or manganese ions is (0.5 to 1.5):1; the concentration ratio of cobalt and manganese ions is 1:(0.3 to 1.2); the ratios of the total of the concentrations of cobalt and manganese ions and the concentration of the bromine ions is 1:(0.1 to 1);

and the total of the concentrations of cobalt and manganese ions is 0.02 to 0.15 mol per 1 of liquid phase.

18. The process as claimed in claim 17, wherein said ratio of the total concentrations of cobalt and manganese ions is 1:(0.2 to 0.7), and said total of the concentrations of cobalt and manganese ions is 0.04 to 0.12 mol.

19. The process as claimed in claim 7, wherein said oxygen partial pressure is 2.4 to 7 bar, and wherein the reaction temperature is 130° to 180° C.

20. A process for the preparation of an alkanesulfonylbenzoic acid from an alkanesulfonylalkybenzene, which process comprises:

oxidizing an alkanesulfonylalkylbenzene of the formula I

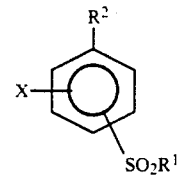

in which $R^1$ and $R^2$ are identical or different and are alkyl having 1 to 4 carbon atoms, but $R^2$, the group which is oxidized, has a meaning other, than t-butyl, and X is H, F, Cl, Br or $NO_2$, with molecular oxygen in acetic acid or propionic acid or mixtures thereof in the presence of a catalyst containing cobalt ions and bromine ions and which further contains a metal ion of Main Group 2 or Main Group 3 or a combination of ions from Main Groups 2 and 3.

* * * * *

UNITED STATES PATENT AND TRADEMARK OFFICE
CERTIFICATE OF CORRECTION

PATENT NO. : 5,175,351
DATED : December 29, 1992
INVENTOR(S) : Freimund Rohrscheid It is certified that error appears in the above-indentified patent and that said Letters Patent is hereby corrected as shown below:

In claim 3, at column 4, line 20, please insert --1-- between "claim" and "wherein".

In claim 7, at column 4, line 33, please insert --1-- after "claim".

In claim 11, at column 4, line 44, "claim 1" should read --claim 10--.

In claim 13, at column 4, line 53, please insert --of-- before "metal ions".

In claim 14, at column 4, line 56, "then" should read --than--.

In claim 20, at column 6, line 12, please delete the "," after "other".

Signed and Sealed this

Seventh Day of December, 1993

Attest:

BRUCE LEHMAN

*Attesting Officer*  *Commissioner of Patents and Trademarks*